United States Patent
Yumiyama et al.

(10) Patent No.: US 9,615,895 B2
(45) Date of Patent: Apr. 11, 2017

(54) DENTAL POLISHING INSTRUMENT

(71) Applicant: KABUSHIKI KAISHA SHOFU, Kyoto (JP)

(72) Inventors: Naoki Yumiyama, Kyoto (JP); Osamu Asao, Kyoto (JP); Masahiko Iwata, Kyoto (JP); Shuji Sonoi, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 175 days.

(21) Appl. No.: 14/606,344

(22) Filed: Jan. 27, 2015

(65) Prior Publication Data

US 2015/0230883 A1    Aug. 20, 2015

(30) Foreign Application Priority Data

Feb. 18, 2014  (JP) ................... 2014-028172
Sep. 24, 2014  (JP) ................... 2014-194293

(51) Int. Cl.
*A61C 15/04*  (2006.01)
*A61C 3/06*   (2006.01)
*A61C 3/02*   (2006.01)

(52) U.S. Cl.
CPC . *A61C 3/06* (2013.01); *A61C 3/02* (2013.01)

(58) Field of Classification Search
CPC .... A61C 3/02; A61C 3/06; A61C 3/03; A61C 3/12; A61C 17/005; A61C 15/042
See application file for complete search history.

(56) References Cited

U.S. PATENT DOCUMENTS

| | | | |
|---|---|---|---|
| 4,592,729 | A | 6/1986  | Bilciurescu |
| 4,830,615 | A | 5/1989  | Goldstein et al. |
| 5,681,217 | A | 10/1997 | Hoopman et al. |
| 5,910,471 | A | 6/1999  | Christianson et al. |

(Continued)

FOREIGN PATENT DOCUMENTS

| | | |
|---|---|---|
| JP | 6-22983  | 2/1994 |
| JP | 10-99346 | 4/1998 |

(Continued)

OTHER PUBLICATIONS

European Search Report issued May 19, 2015 in corresponding European Patent Application No. 15153009.4.

*Primary Examiner* — Joseph Dietrich
(74) *Attorney, Agent, or Firm* — Wenderoth, Lind & Ponack, L.L.P.

(57) ABSTRACT

An object of the present invention is to provide a dental polishing instrument that causes no clogging, that prevents occurrence of any secondary flaw, that is excellent in the polishing property, and that can provide high gloss in a short time period, for a dental prosthetic appliance difficult to polish. Another object thereof is to provide a dental polishing instrument that enables easy discharge of polishing sludge while that simultaneously shows sufficient strength. A dental polishing instrument according to the present invention can suppress clogging and occurrence of any secondary flaw due to the polishing sludge and can efficiently polish by forming a polishing abrasive grain layer including polishing abrasive grains and a resin material, into protrusions on the surface of a base material thereof and by disposing the protrusions on the base material.

12 Claims, 7 Drawing Sheets

(56) References Cited

U.S. PATENT DOCUMENTS

2009/0068614 A1\* 3/2009 Sonoi .................. B24D 3/32
          433/166
2011/0256504 A1 10/2011 Rudman

FOREIGN PATENT DOCUMENTS

| JP | 2001-9736 | 1/2001 |
| JP | 2005-22033 | 1/2005 |

\* cited by examiner

DENTAL POLISHING INSTRUMENT

TECHNICAL FIELD

The present invention relates to a dental polishing instrument capable of efficiently executing polishing work for a dental prosthetic appliance such as a composite resin or a porcelain, and capable acquiring high gloss.

BACKGROUND ART

During execution of dental treatment, when a tooth suffers a disease such as dental caries, the affected portion is removed, and restoration treatment is executed using various prosthetic materials such as a metal, a dental composite resin, and a porcelain.

The dental prosthetic appliance needs to undergo surface polishing after modification of its shape. When the polished surface is rough or when a flaw is present therein, this causes coloring, and adhesion of dental plaque. When the surface of the prosthetic appliance is not smooth and glossy, high aesthetics cannot be acquired and the touch felt by the tongue of a patient is bad. Therefore, the patient may feel uncomfortable.

Recently, cases of restoration treatment using materials having higher aesthetics such as the dental composite resin and ceramic materials including the porcelain have increased because of the growth of the demand for aesthetics by the patients. However, these materials are materials difficult to polish, and are highly difficult to polish. For example, the dental composite resin includes a glass filler having high hardness and a resin having low hardness. A substance including plural composition components each having hardness different from each other as above is difficult to evenly polish, and causing the substance to have gloss in the final polishing stage is highly difficult. A ceramic material includes, in its configuring materials, raw materials such as minerals such as feldspar and quartz, or leucite, alumina, zirconia, and lithium disilicate. This material has high aesthetics and durability that maintains the aesthetics for a long time, and is therefore introduced mainly into self-pay treatment. The material however has a highly hard physical property to maintain its high durability. Therefore, the ceramic material is classified as a material difficult to polish.

At present, the polishing is executed using various polishing instruments after adjusting the shape and the articulation of the dental prosthetic appliance using an abrasive material including vitrified or electro-deposition diamond. The polishing is executed using, for example, a point type polishing instrument formed by mixing polishing abrasive grains and an elastomer-based binder resin and shaping the mixture in a point shape, a disc type polishing instrument formed by fixing polishing abrasive grains to a disc-shaped base material, or a sheet type polishing instrument formed by adhering polishing abrasive grains to the surface of a rectangular shaped sheet.

In a dental clinic, as to the above polishing instruments, a doctor selects a proper polishing instrument from the various types of polishing instrument corresponding to the case. For example, the disc type polishing instrument has a highly effective shape for polishing a flat portion such as the surface of a front tooth facing a lip because the disc type polishing instrument is in evenly contact with the flat portion. The sheet type polishing instrument has a rectangular shape suitable for polishing an interdental portion (adjacent surfaces), and polishing is executed by placing the instrument through the interdentium and causing the polishing layer to be in contact with the adjacent surfaces. For a molar, the point type polishing instrument is effective such as that having a bullet shape suitable for polishing a complicated-shaped portion. Types of these polishing instruments include one having a polishing layer and a shaft integrated with each other and a snap-on type one including a shaft detachable unit capable of being attached and detached to/from the shaft to be used in dental clinical duties.

However, sufficient gloss cannot be acquired using any of these methods and, after using any one of the above polishing instruments, the final polishing gives the gloss by puff polishing using a dedicated polishing paste. However, this polishing work needs a long time and the polishing steps are increased. Therefore, the treatment efficiency is low and the chair time is extended imposing loads on both of the operator and the patient. These problems similarly arise in the dental technical work. When the polishing work takes a long time, the load on the operator due to the increase of the working time period becomes significant. Therefore, a polishing instrument achieving a high polishing effect is demanded to reduce the working time period.

Patent Literature 1 discloses a technique of improving a polishing property by kneading fine ultra abrasive grains such as diamond in an elastic elastomer, fitting the kneaded mixture with a surface to be polished, and reducing vibrations generated during the polishing. Patent Literature 2 discloses a technique concerning a dental polishing instrument whose polishing property is improved by forming the instrument as a curved disc-shaped polishing instrument to cause the instrument to fit with not only a flat surface but also a curved tooth surface.

The polishing instruments according to the techniques described in Patent Literature 1 and Patent Literature 2 each improve the polishing property by causing its polishing layer to fit with the surface to be polished. In each of Patent Literature 1 and Patent Literature 2, however, a mechanism is not properly provided that causes the polishing sludge produced during the polishing to leave and no sufficient polishing effect tends to be acquired due to occurrence of a secondary flaw caused by clogging or continuous contact of the polishing sludge with the surface to be polished.

On the other hand, to solve the problem, a technique is disclosed of disposing an air hole portion that intentionally causes the polishing sludge to leave. For example, Patent Literature 3 discloses a technique of improving the polishing property by disposing recesses or holes in a polishing layer, reducing the friction heat produced during the polishing, and causing the polishing sludge to leave. However, the recesses or the holes are disposed in only a portion of the polishing instrument, and the removing effect is high for the polishing sludge concerning the polishing layer close to the recesses or the holes while this effect is degraded for the polishing layer far from the recesses or the holes. According to Patent Document 3, therefore, as a result, the occurrence of the secondary flaw due to the clogging or the polishing sludge is inevitable.

Patent Literature 4 discloses a technique concerning a disc (sheet)-shaped polishing instrument whose polishing layer has air holes formed therein and that can maintain a polishing effect by constant emergence of a newly produced surface. According to Patent Literature 4, however, the formed air holes are unable to be controlled to always have the same positions and the same size depending on the casting condition. The acquired polishing effect presents an individual difference and cannot be said to be stable.

Because the air holds are disposed in the polishing layer, the clogging and occurrence of the secondary flaw due to the polishing sludge may be suppressed while the strength of the polishing instrument may be degraded.

CITATION LIST

Patent Literature

PLT 1: Japanese Laid-Open Patent Publication No. 6-22983
PLT 2: Japanese Laid-Open Patent Publication No. 10-99346
PLT 3: Japanese Laid-Open Patent Publication No. 2005-22033
PLT 4: Japanese Laid-Open Patent Publication No. 2001-9736

SUMMARY OF INVENTION

Technical Problem

An object of the present invention is to provide a dental polishing instrument that causes no clogging by the polishing sludge, that prevents occurrence of any secondary flaw, that is excellent in the polishing property, and that gives high gloss in a short time period, for a dental prosthetic appliance difficult to polish such as a dental composite resin and ceramic materials including a porcelain. Another object thereof is to provide a dental polishing instrument that enables easy discharge of the polishing sludge while that presents sufficient strength.

Solution to Problem

A dental polishing instrument according to an aspect of the present invention having a polishing layer mounted on a base material, includes
the base material that forms a mother body,
the polishing layer that is disposed on a surface of the base material,
protrusions that are disposed on a surface of the polishing layer,
wherein the protrusions are each formed independently from each other being raised,
wherein each of the protrusions has a height of 20 μm to 80 μm, and has an oval shape when viewed from top,
wherein a length of a longer diameter and a shorter diameter of the oval shape of each of the protrusions is 20 μm to 100 μm, and the length of the shorter diameter is 80% to 100% relative to the length of the longer diameter, and
wherein a rate of occupancy by the protrusions per unit area in the polishing layer is 40% to 90%.

Advantageous Effects of Invention

The dental polishing instrument according to the present invention causes no clogging by the polishing sludge produced during the polishing and can reduce the cases of occurrence of any secondary flaw due to the polishing sludge even when the dental polishing instrument polishes a dental prosthetic appliance that is difficult to polish. The dental polishing instrument according to the present invention achieves a high polishing effect, therefore, can give high gloss in a short time to the dental prosthetic appliance, and can reduce the load imposed on the operator and the patient. The dental polishing instrument according to the present invention tends to cause no clogging by the polishing sludge, achieves a high polishing effect, and also has a sufficient mechanical strength.

DESCRIPTION OF EMBODIMENTS

Figure 1:
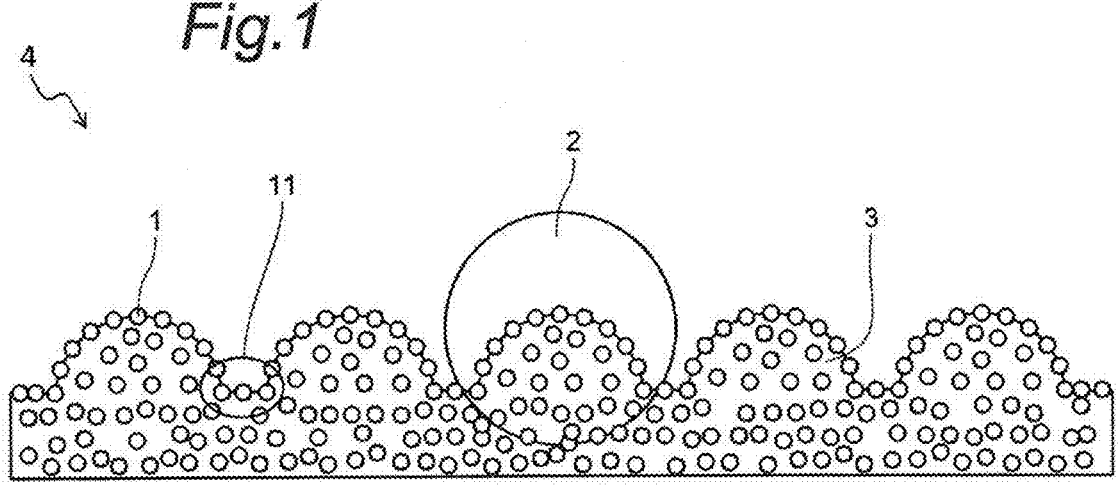
FIG. 1 is a schematic cross-sectional diagram of a polishing layer of a dental polishing instrument according to the present invention.

A dental polishing instrument according to a first aspect of the present invention having a polishing layer mounted on a base material may include: the base material that forms a mother body; the polishing layer that is disposed on a surface of the base material; and protrusions that are disposed on a surface of the polishing layer, wherein the protrusions are each formed independently from each other, wherein each of the protrusions has a height of 20 μm to 80 μm, and has an oval shape when viewed from top, wherein a length of a longer diameter and a shorter diameter of the oval shape of each of the protrusions is 20 μm to 100 μm, and the length of the shorter diameter is 80% to 100% of the length of the longer diameter, and wherein a rate of occupancy by the protrusions per unit area in the polishing layer is 40% to 90%.

A dental polishing instrument according to a second aspect of the present invention may include flat portions (non-protruding portions) between the protrusions that have no protrusion formed thereon, on the surface of the polishing layer of the first aspect, and the flat portions may contiguously be connected to each other.

A dental polishing instrument according to a third aspect of the present invention may include the polishing layer according to the first aspect that includes polishing abrasive grains and a binder resin. The polishing abrasive grains includes one or more compounds selected from alumina, zirconia, silicon carbide, diamond, silica, calcium carbonate, cerium oxide, and boron nitride, and has the granularity of #400 to #8000 at a content of 30 to 90 weight parts relative to 100 weight parts of the polishing layer. The binder resin includes one or more resin(s) selected from polyester-based resins, epoxy-based resins, and polyurethane-based resins at a content of 10 to 70 weight parts relative to 100 weight parts of the polishing layer.

A dental polishing instrument according to a fourth aspect of the present invention may include the protrusions according to the third aspect that include a mixture of the polishing abrasive grains and the binder resin.

A dental polishing instrument according to a fifth aspect of the present invention may include the base material of the first aspect that has a disc shape with a diameter of 4 mm to 16 mm and a thickness of 0.050 mm to 0.150 mm, and has the polishing layer on its one flat surface, and also has a connecting portion for connecting to a shaft of a driver.

A dental polishing instrument according to a sixth aspect of the present invention may have another polishing layer disposed on another surface of the disc-shaped base material of the fifth aspect.

A dental polishing instrument according to a seventh aspect of the present invention may include the base material of the first aspect that has a shape of a column body with a front surface and a bottom surface.

A dental polishing instrument according to an eighth aspect of the present invention may include the base material of the first aspect that has a shape of a conical body with a front surface and a bottom surface.

A dental polishing instrument according to a ninth aspect of the present invention may include the base material of the first aspect that has a shape of a parabola revolution body with a front surface and a bottom surface.

A dental polishing instrument according to a tenth aspect of the present invention may include the base material of the first aspect that has a bullet shape with a front surface and a bottom surface.

A dental polishing instrument according to an eleventh aspect of the present invention may include the base material of any one of the seventh to the tenth aspects that has a largest diameter of 2 mm to 20 mm and a height of 5 mm to 40 mm, and has the polishing layer disposed on the front surface, and has a connecting portion for connecting to a shaft of a driver on the bottom surface.

A dental polishing instrument according to a twelfth aspect of the present invention may include the base material of the first aspect that has a rectangular shape with a shorter side being 1 mm to 10 mm and the longer side being 10 mm to 50 m, and has the polishing layer on one or both surfaces thereof.

The present invention is described below with reference to the accompanying drawings. In all the drawings below, the same or the corresponding parts are given the same reference numerals and are not again be described.

FIG. 1 is a schematic cross-sectional diagram of a polishing layer of a dental polishing instrument according to the present invention. As shown in FIG. 1, the polishing layer 4 of the dental polishing instrument according to the present invention includes polishing abrasive grains 1 and a binder resin 3. A surface to be in contact with an object to be polished of the polishing layer 4 has plural protrusions 2 and non-protruding portions (flat portions) 11 formed thereon. The protrusions 2 are formed being raised to be in a convex shape in the surface direction to be the direction toward the object to be polished from the surface of the polishing layer 4 including the polishing abrasive grains 1 and the binder resin 3. The non-protruding portions, that is, the flat portions 11 are portions between the protrusions 2 having no protrusions 2 formed thereon. The non-protruding portions 11 are formed being contiguously connected to each other. The "direction toward the object to be polished" means a direction indicating the presence of the object to be polished that is a target object of the polishing.

Figure 2:
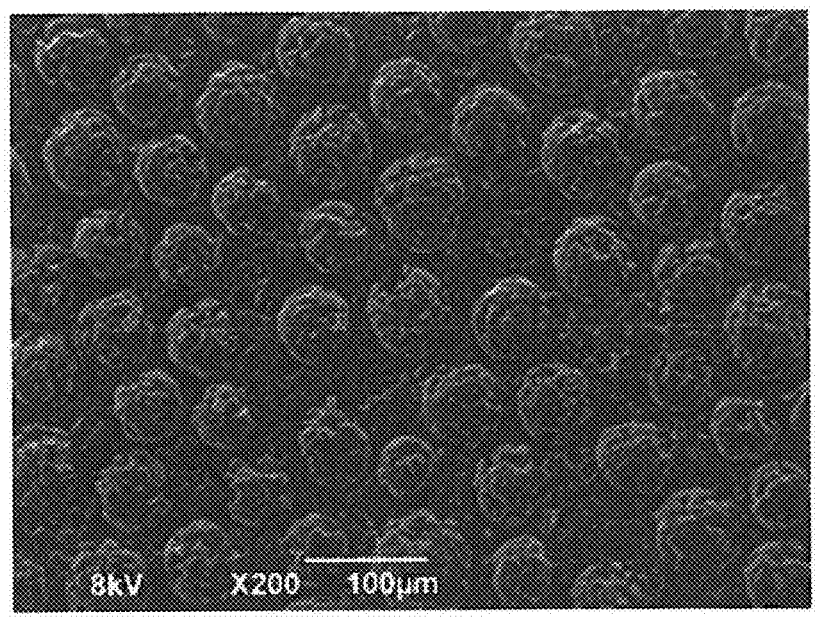
FIG. 2 is an SEM (Scanning Electron Microscope) image of the polishing layer of the dental polishing instrument according to the present invention.

FIG. 2 is an SEM (Scanning Electron Microscope) image of the polishing layer of the dental polishing instrument according to the present invention. As shown in FIG. 2, the protrusions 2 of the polishing layer 4 of the present invention each has, for example, a semi-oval spherical shape (an oval shape when viewed from top) and are each disposed independently from each other on the surface of the polishing layer 4. The protrusions 2 may regularly be disposed on the surface of the polishing layer 4 or may randomly be disposed thereon.

Figure 3:
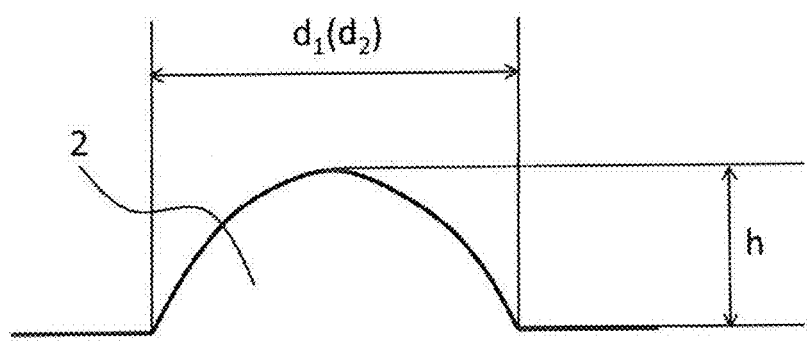
FIG. 3 is a diagram for explaining a definition of a height of each of protrusions of the polishing layer.

FIG. 3 is a diagram of a definition of a height of the protrusion 2 acquired when the protrusion 2 is seen from the side. The "height h of the protrusion 2" as used herein means a length from the non-protruding portion 11 having no protrusion 2 formed thereon on the surface of the polishing layer 4 to the apex of the protrusion 2, as shown in FIG. 3.

Figure 4:
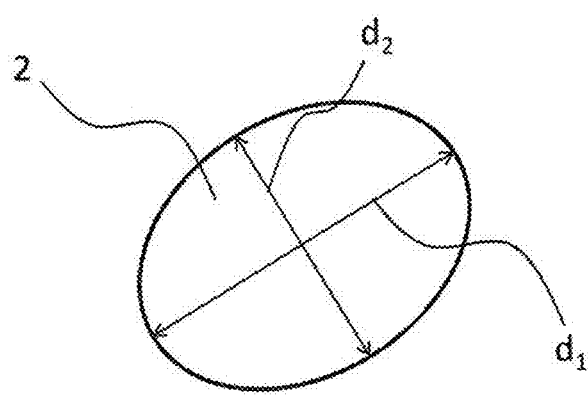
FIG. 4 is a diagram for explaining definitions of a longer diameter and a shorter diameter of the protrusions of the polishing layer.

FIG. 4 is a diagram of definitions of a longer diameter and a shorter diameter of the protrusion 2 acquired when the protrusion 2 is seen from top. The "longer diameter $d_1$ of the protrusion 2" as used herein means a diameter of the longest portion acquired when the protrusion 2 is seen from top, as shown in FIG. 4. The "shorter diameter $d_2$ of the protrusion 2" as used herein means, as shown in FIG. 4, a diameter of the shortest portion of the protrusion 2 acquired when the protrusion 2 is seen from top.

Figure 5:
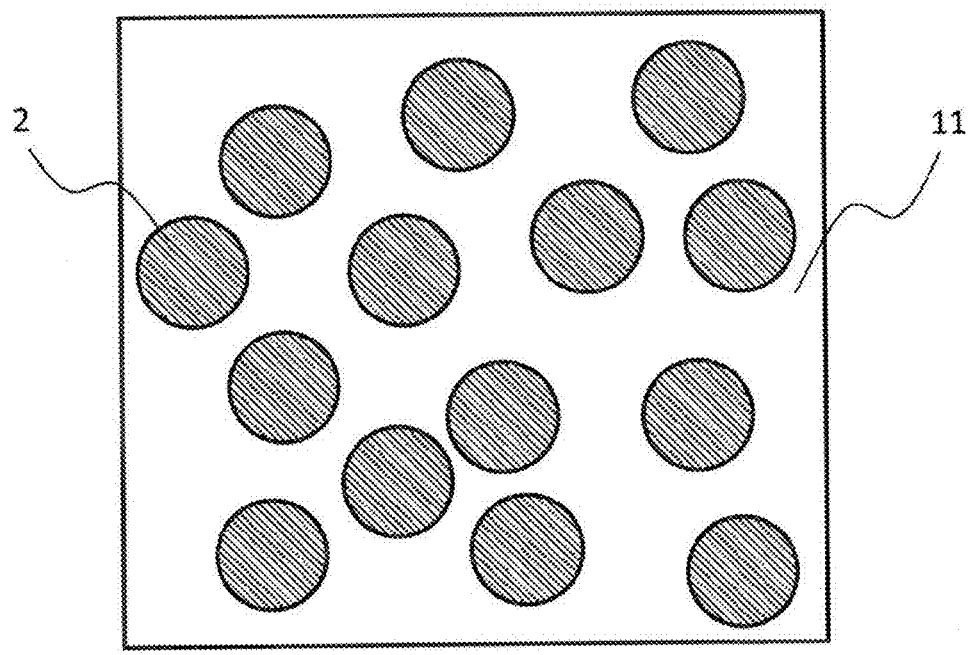
FIG. 5 is a diagram for explaining a definition of a rate of occupancy by the protrusions in the polishing layer.

The protrusion 2 is raised in the surface direction that is the direction indicating the object to be polished. The height h of the protrusion 2 is selected from a range from 20 μm to 80 μm, and the longer diameter $d_1$ and the shorter diameter $d_2$ of the protrusion 2 are selected from a range from 20 μm to 100 μm. More preferably, the height h of the protrusion 2 desirably is 35 μm to 50 μm, and the longer diameter $d_1$ and the shorter diameter $d_2$ of the protrusion 2 desirably are 30 μm to 70 μm. An example shows that the length of the shorter diameter $d_2$ of the protrusion 2 is 80% to 100%, or preferably 80% to 97%, relative to the length of the longer diameter $d_1$. The non-protruding portions of the polishing layer 4 are contiguously connected to each other. The casting is executed such that the rate of occupancy by the protrusions 2 per unit area is 40% to 90% and, more preferably, is 50% to 80%. The "rate of occupancy by the protrusions 2 per unit area" means the rate of the area of the protrusions 2 (shaded portions of FIG. 5) occupying in the unit area of the polishing layer 4, as shown in FIG. 5. The shape of the protrusion 2 is not especially limited. Preferably, the shape can be such as a semispherical shape, a semi-oval sphere, a conical body, or a column body and, more preferably, desirably is a semispherical protrusion.

The protrusions 2 are designed such that the polishing sludge produced during the polishing of the dental prosthetic appliance is properly discharged. Therefore, this causes no clogging, can prevent occurrence of any secondary flaw due to the polishing sludge, and can suppress occurrence of any friction heat produced by the polishing. The polishing effect is high, and this causes high gloss to be acquired in a short time period and reduces the loads imposed on the operator and the patient. The polishing instrument of the present invention causes no recess or no air hole to be disposed in the polishing layer like the traditional techniques, and strength can therefore be provided that is sufficient for clinical treatment.

Figure 6:
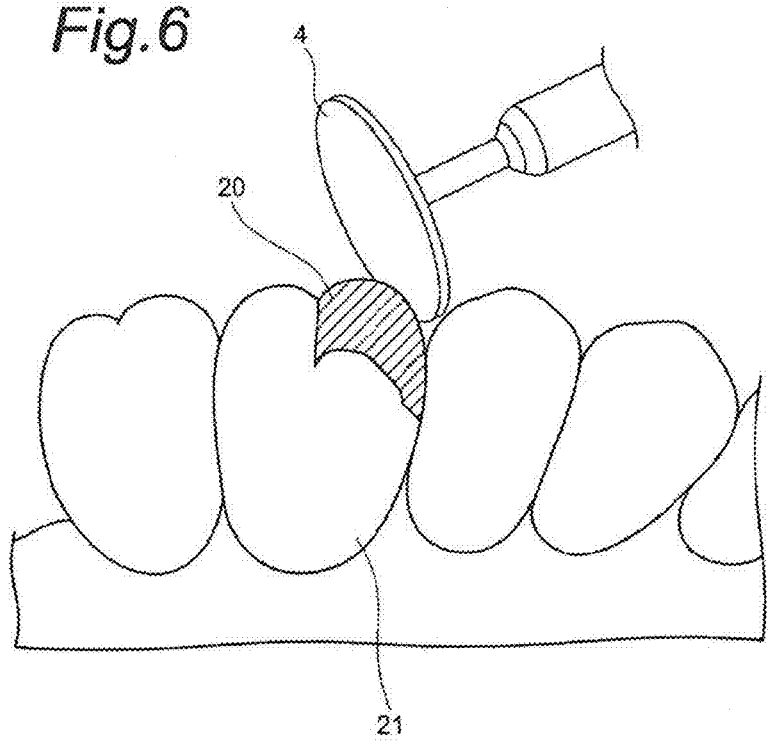
FIG. 6 is a diagram for explaining a state where the dental polishing instrument polishes a dental prosthetic appliance in a mouth orifice.

FIG. 6 is a diagram of a state where a dental prosthetic appliance 20 in a mouth orifice is polished using the dental polishing instrument according to the present invention. As shown in FIG. 6, the dental prosthetic appliance 20 restores the portion lost from a natural tooth 21 due to dental caries, etc. The dental prosthetic appliance is manufactured using various materials such as a composite resin, a porcelain (a ceramic material), and a metal, and its material property such as hardness therefore significantly differs depending on its material. The dental polishing instrument according to the present invention is used being attached to the rotating polishing machine. The polishing instrument according to the present invention is rotated by the rotating polishing machine. The polishing layer 4 of the rotating dental polishing instrument is brought into contact with the dental prosthetic appliance and, thereby, the dental prosthetic appliance can be polished. The polishing instrument according to the present invention can polish any one material of a composite resin, a porcelain (a ceramic material), and a metal by changing the polishing abrasive grains. The polishing abrasive grains 1 used in the polishing layer 4 of the present invention are selected from #400 to #8000 and, preferably, those having the granularity of #1000 to #4000 are used. Preferably, one or more compound(s) is/are selected as the type of the polishing abrasive grains 1 from alumina, zirconia, silicon carbide, diamond, silica, calcium carbonate, cerium oxide, and boron nitride. For the dental polishing instrument according to the present invention, optimal compounds may be selected as the polishing abrasive grains 1 and the binder resin 3 of the polishing layer 4 corresponding to the material of the prosthetic appliance. Therefore, one or more compound(s) may be selected as the polishing abrasive grains 1 of the polishing layer 4 of the present invention from the above types of the polishing abrasive grains corresponding to the compound property of the object to be polished. More preferably, white fused alumina or artificial diamond is selected for the polishing instrument to especially polish a dental composite resin and a ceramic material. These types of polishing abrasive grains can also be combined.

A polyester-based, an epoxy-based, or a polyurethane-based resin material can advantageously be used as the binder resin 3 used in the polishing layer 4. More preferably, a polyester-based resin can be used.

The polishing layer 4 including the protrusions 2 is formed from an item including the polishing abrasive grains 1 and the binder resin 3 and, preferably, is desirably formed from a mixture including the polishing abrasive grains 1 and the binder resin 3. For the polishing layer 4, the blending is executed for the polishing abrasive grains 1 to be in a range from 30 to 90 weight parts and the binder resin 3 to be in a range from 10 to 70 weight parts. Preferably, the weight ratios of the polishing abrasive grains 1 and the binder resin 3 are between 3:7 and 9:1. More preferably, the blending ratios of the polishing abrasive grains 1 and the binder resin 3 are 50 weight parts for the polishing abrasive grains 1 and 50 weight parts for the binder resin 3.

In the process of forming the polishing layer 4, when the polishing abrasive grains 1 and the binder resin 3 are mixed, a dilution solvent may be used when necessary. A hardening agent may be blended to fix the polishing abrasive grains 1 to the binder resin 3. The hardening agent can be an isocyanate-based hardening agent, an aminoplast-based hardening agent, or a polyepoxy compound.

The polishing instrument according to the present invention includes a base material and the polishing layer 4, and the polishing layer 4 is disposed on the base material. For example, the polishing layer 4 is disposed on the front surface of the base material and, preferably, the polishing layer 4 is adhered by an adhesive to the front surface of the base material.

The polishing instrument can be formed as a polishing instrument whose base material and a shaft are integrated with each other, or a snap-on type polishing instrument having on the base material a shaft detachable unit that is attachable and detachable to/from the shaft. The polishing instrument can thereby be used by being attached to the rotating polishing machine such as a dental hand piece and being rotated thereby. In this case, the shaft and the shaft detachable unit are positioned in a rotating shaft of the polishing instrument. The "rotating shaft" means a portion of the shaft to be the rotation center when the polishing instrument is rotated. When the base material and the shaft are integrated with each other, the base material and the shaft can be adhered to each other using an adhesive when necessary.

The base material can be shaped into an arbitrary shape corresponding to the purpose of the polishing. For example, the shape can be a disc shape, a point shape, or a rectangular shape while the shape is not especially limited. Preferably, among these, the disc shape or the point shape is used when the polishing instrument is attached to the dental hand piece.

Figure 7:
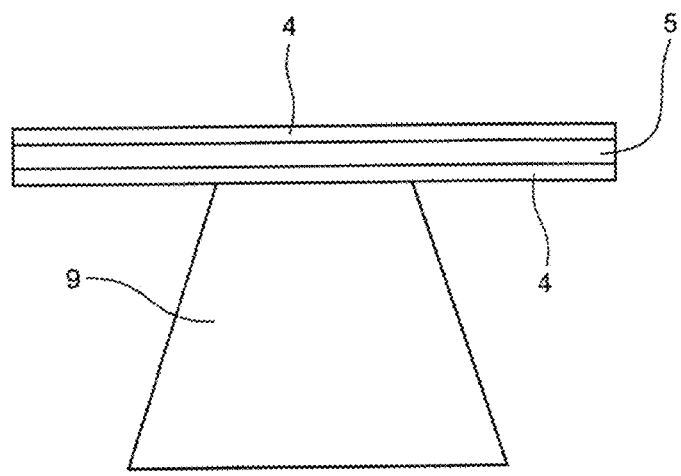
FIG. 7 is a schematic diagram of a disc type polishing instrument according to the present invention.

FIG. 7 is a schematic diagram of a polishing instrument including a disc-shaped base material. As to the disc-shaped base material 5, preferably, the diameter of the disc-shaped base material 5 is selected from a range from 4 mm to 16 mm and the thickness thereof is selected from a range from 0.050 mm to 0.150 mm and, more preferably, the diameter desirably is 8 mm to 12 mm and the thickness desirably is 0.075 mm to 0.125 mm. The disc-shaped base material 5 has the polishing layer 4 disposed on either the one or the other surface, or each of both surfaces thereof, and a connecting portion (a soft block) 9 connecting to the shaft connected to a driver is disposed on the surface(s).

The disc type polishing instrument manufactured using the disc-shaped base material 5 can realize its proper bowing and is in contact evenly with a flat portion when the polishing instrument polishes the flat portion such as the surface of a front tooth facing a lip. The polishing instrument therefore is highly effective for polishing a flat surface. The disposition of the polishing layer 4 on either the one or the other surface, or both surfaces of the disc-shaped base material 5 enables polishing from both sides in the proximal and distal directions for the adjacent surfaces that form an interdental portion.

Figure 8:
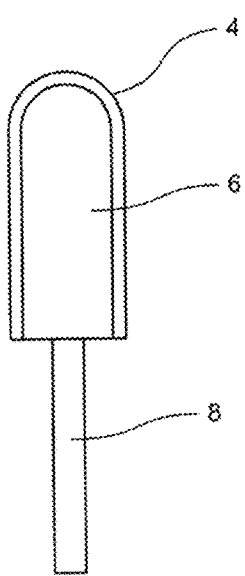
FIG. 8 is a schematic diagram of a point type (bullet type) polishing instrument according to the present invention.

FIG. 8 shows a schematic diagram of the polishing instrument including the point-shaped base material. As to the point-shaped base material 6, the base material 6 can be shaped into a point shape having a shape selected from a column body, a conical body, a parabola revolution body, and a bullet shape. Preferably, the largest diameter of the point-shaped base material 6 is selected from a range from 2 mm to 20 mm and the height thereof is selected from a range from 5 mm to 40 mm and, more preferably, the largest diameter desirably is 4 mm to 15 mm and the height desirably is 8 mm to 20 mm. Preferably, the rubber hardness of the point-shaped base material 6 is 80 to 95 of the "JIS A" scale to supply proper elasticity thereto. The polishing layer 4 is disposed on the surface of the point-shaped base material 6, and a shaft 8 connecting to the driver is disposed on the other surface such as the bottom surface.

The point type polishing instrument manufactured using the point-shaped base material 6 can cope with polishing of a complicated shape such as an articulation surface or a fissure portion and is, therefore, especially effective for molars.

Figure 9:
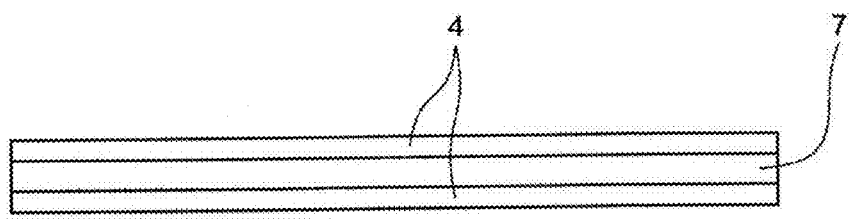
FIG. 9 is a schematic diagram of a sheet type (rectangular type) polishing instrument according to the present invention.

FIG. 9 is a schematic diagram of the polishing instrument including the rectangular shaped base material. When the rectangular shaped base material 7 is employed as the base material, preferably, the shorter side length is selected from a range from 1 mm to 10 mm and the longer side length is selected from a range from 10 mm to 50 m, and the base material 7 can also be used after cutting the longer side into a necessary length. The sheet-shaped polishing instrument including the polishing layer 4 on the one or each of both surfaces of the rectangular shaped base material 7 is suitable for polishing the interdental portion (the adjacent surfaces). To facilitate the polishing work, a handle to hold the polishing instrument can also be attached thereto.

When the rectangular shaped base material 7 is used, forming the point shape is enabled by disposing the polishing layer 4 on the one surface of the rectangular shaped base material 7 and executing winding-up casting after setting the polishing layer 4 to be on the outer surface. In this case, preferably, the longer side length of the rectangular shaped base material 7 is 30 mm to 200 mm and the shorter side length thereof is 1 mm to 30 mm.

The material of each of the three types of base material may be arbitrarily determined. For example, a base material formed by shaping that of polyethylene-terephthalate, nonwoven cloth, paper, or Tetron taffeta into a sheet may be used, and an elastomer-based binder having rubber elasticity may be employed. The elastomer-based binder only has to be at least one type of synthetic rubber or natural rubber such as silicone rubber, urethane rubber, chloroprene rubber, nitrile rubber, butadiene rubber, butyl rubber, styrene-butadiene rubber, ethylene-propylene rubber, and fluorine-containing rubber and, preferably, silicone rubber or urethane rubber is used. For example, for the disc-shaped base material 5 and the rectangular shaped base material 7, preferably, the base material of polyethylene-terephthalate, etc., shaped into a sheet is used. For the disc-shaped base material 5, a base material is used that is formed by cutting a sheet-shaped base material into the disc-shaped base material. For the rectangular shaped base material 7, a base material is used that is formed by cutting a sheet-shaped base material into the rectangular shaped base material. For the point-shaped base material 6, a base material is used that is formed by casting an elastomer-based binder into a point shape such as a column body, a conical body, a parabola revolution body, or a bullet shape. These base materials each form a mother body of the dental polishing instrument.

Figure 10:
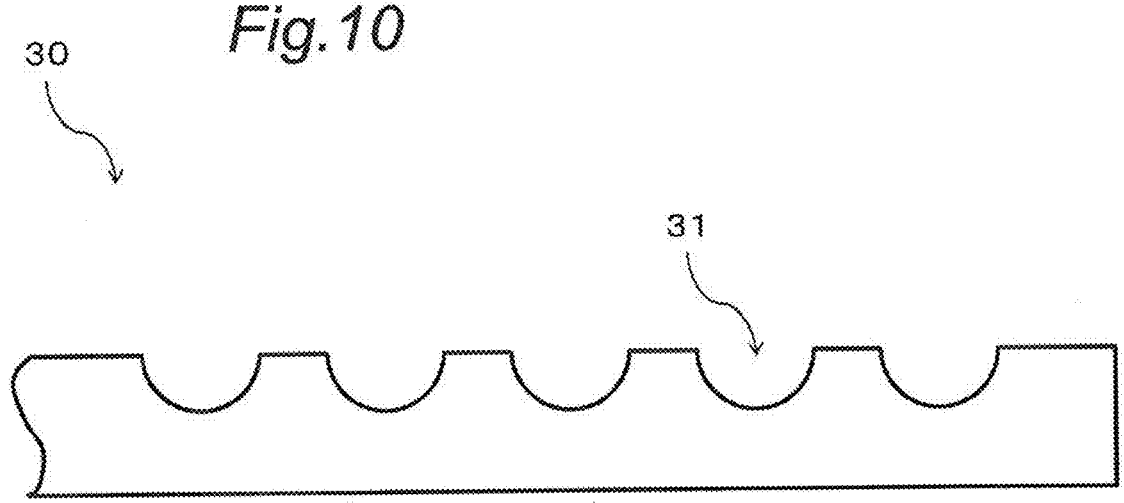
FIG. 10 is a schematic diagram of a mold sheet (a mold).

The manufacture method of the dental polishing instrument according to the present invention may be arbitrarily determined. However, a manufacture method of the dental polishing instrument using a mold sheet is described as an example. FIG. 10 is a schematic diagram of a mold sheet. The mold sheet 30 shown in FIG. 10 includes plural recesses 31. The plural recesses 31 each has a shape such as a semispherical shape, a semi-oval sphere, a conical body, or a column body to determine the shape of each of the protrusions 2 of the polishing layer 4, for example.

The polishing abrasive grains 1 and the binder resin 3 are mixed (step ST1). The mixture including the polishing abrasive grains 1 and the binder resin 3 is poured into the mold sheet (a mold) 30 provided with the recesses 31 (see FIG. 10) (step ST2). The resin (the binder resin 3) included in the mixture is hardened to form the polishing layer 4 including the predetermined protrusions 2 (step ST3). A sheet-shaped auxiliary material may also be used when necessary to maintain the shape of the polishing layer 4. For example, the shape of the polishing layer 4 can be maintained by closely attaching the auxiliary material and hardening the resin prior to step ST3 to harden the mixture including the polishing abrasive grains 1 and the binder resin 3 during the manufacture of the polishing layer 4.

The polishing layer 4 can also be formed by placing the polishing abrasive grains 1 on the mold sheet (the mold) 30, pouring the binder resin 3 thereon, and hardening the resin (the binder resin 3) included in the mixture, as a method of adhering the polishing abrasive grains 1 to the surface of the polishing layer 4.

The polishing layer 4 is detached from the mold sheet 30 (step ST4). The detached polishing layer 4 and the base material are adhered to each other (step ST5). The base material and the polishing layer 4 are adhered to each other by forming a primer layer by a primer process on the base material formed into an arbitrary shape and executing hot pressing therefor. For the primer layer, a material can be used that is selected from an acrylic resin, a polyethylene-based resin, a urethane-based resin, and a rubber-based resin. For example, when polyethylene-terephthalate is used for the base material, a polyurethane-based resin is desirably used as the primer. For example, the primer layer is formed by applying to the base material surface a blended solution including 100 weight parts of the polyurethane-based resin and five weight parts of a modified polyisocyanate resin as the hardening agent, and drying the blended solution using hot air. The polishing layer 4 is adhered by applying an adhesive on the primer layer of the base material and, thereby, the dental polishing instrument of the present invention can be manufactured.

For the point type polishing instrument, the predetermined polishing instrument can also be manufactured by manufacturing the point-shaped base material by casting using an elastomer-based binder mold and, thereafter, pressure-boding the point-shaped base material with the polishing layer 4.

The "direction toward the object to be polished of the base material" as used herein refers to the direction toward the dental prosthetic appliance that is the material to be polished for the dental polishing instrument.

The "protrusions 2 are each independent" represents that the protrusions 2 are each raised toward the highest portion to be the apex of the protrusion 2 without having therein any inflection point in the direction toward the non-protruding portions, and the protrusions 2 each are not newly raised without reaching the non-protruding portion in a specific direction. This is not applicable to any recess or protrusion cased by forming unevenness, etc.

EXAMPLE

An example of embodiments of the present invention is described below with reference to Examples. The embodiments described below do not limit the present invention.

First Embodiment

In the first embodiment, the case is described where a dental composite resin is polished using the disc type polishing instrument that is an aspect of the dental polishing instrument according to the present invention.

Examples of the disc type polishing instrument are described.

(1) Manufacture of Disc Type Polishing Instrument

Examples and Comparative Examples of the disc type polishing instrument were manufactured as below.

For the polishing layer 4, the polishing abrasive grains 1 and the binder resin 3 were mixed at the blending ratios of 50%:50%. In this case, white fused alumina was used as the polishing abrasive grains 1 and their particle diameter was #2000. A polyester-based resin material was employed as the binder resin 3. An isocyanate-based hardening agent was in addition blended as the hardening agent. The blending was executed to set the practical blending ratios to be 100 weight parts of the polyester-based resin, 5 weight parts of hardening agent, and 100 weight parts of the white fused alumina. 75 weight parts of a dilution solvent was further blended to facilitate the mixing and a mixer was used for mixing these.

The mixture was applied to the mold sheet (the mold) 30 manufactured in advance using a top reverse coater (a coating machine) and was hardened. After the hardening, the polishing layer 4 was detached from the mold sheet 30 and, thereby, the final polishing layer 4 was acquired. A polyethylene-terephthalate (PET) piece having a disc shape with a thickness of 0.75 mm and $\phi$ (a diameter) of 12 mm was used as the base material 5. A blended solution including 100 weight parts of a polyurethane-based resin and 5 weight parts of a modified polyisocyanate resin as the hardening agent was applied to the PET piece and was dried using a hot air dryer to form the primer layer having a thickness of 0.05 mm on the base material. Therefore, the overall thickness of this base material was 0.125 µm including that of the primer layer. The polishing layer 4 and the base material 5 having the primer layer formed thereon were brought into contact with each other, and hot pressing was applied thereto to fix the polishing layer 4 and the base material 5 to each other. The soft block 9 (see FIG. 7) as the connecting portion connecting to the shaft connected to the driver was manufactured using polyvinylchloride. This soft block 9 and the base material 5 were fixed to each other using a urethane-based adhesive to acquire the disc type polishing instrument.

(2) Examples and Comparative Examples

The manufactured Examples and Comparative Examples of the disc type polishing instrument are presented in Table 1.

In Example 1 (Ex1), the height h of the protrusions 2 was 42 µm, the longer diameter $d_1$ and the shorter diameter $d_2$ of the protrusions 2 were each 42 µm, the shape of the protrusion 2 was a semispherical body, and the rate of occupancy by the protrusions 2 was 70% per unit area. In Example 2 (Ex2), the height h of the protrusions 2 was 60 µm, the longer diameter $d_1$ and the shorter diameter $d_2$ of the protrusions 2 were each 60 µm, the shape of the protrusion 2 was a semispherical body, and the rate of occupancy by its protrusions 2 was 50% per unit area. Comparative Examples 1 to 4 (Comp1 to Comp4) of the first embodiment were manufactured using the same manufacture method as above.

(3) Evaluation Method for Degree of Gloss

The manufactured disc type polishing instrument was attached to a dedicated mandrel and polished the surface of a test piece of a dental composite resin for 30 sec applying a load of about 1 N at 10,000 $\min^{-1}$, and the degree of gloss acquired in this case was evaluated. The test piece was manufactured according to the following procedure. A stainless ring having an inner diameter of 15 mm and a thickness of 2 mm was placed on a glass slide, and a dental composite resin (Beauty Fill 2, Shofu Inc.) was poured to fill the ring. Another glass slide was further placed thereon and polymerization was executed from both sides for 3 min using a dental optical polymerization vessel (Twincure, Shofu Inc.), and the roughness of the surfaces was set to be a specific roughness using a water resistant polishing paper sheet of #600 to acquire a cylindrical test piece. The degree of gloss of the polished surface of the test piece was measured using a mirror gloss degree measurement method of JIS Z 8741.

In Comparative Example 1 (Comp1), compared to Examples 1 and 2 (Ex1 and Ex2), the height h of the protrusions 2 was high and the longer diameter $d_1$ and the shorter diameter $d_2$ were long, and therefore no clogging occurred while the contact area between the test piece and the protrusions 2 was small and no sufficient polishing effect was achieved. In Comparative Example 2 (Comp2), compared to Examples 1 and 2, the height h of the protrusions 2 was low and the longer diameter $d_1$ and the shorter diameter $d_2$ were short. Therefore, in Comparative Example 2, the sludge produced during the polishing caused clogging, and no sufficient polishing effect was achieved compared to Examples 1 and 2.

In Comparative Example 3 (Comp3), compared to Examples 1 and 2, the rate of occupancy by the protrusions 2 was low and the area in contact with the surface to be polished was small. Therefore, no sufficient polishing effect was achieved.

In Comparative Example 4 (Comp4), compared to Examples 1 and 2, the rate of occupancy by the protrusions 2 is high and no sufficient interspaces were acquired, and therefore clogging occurred during the polishing similarly to Comparative Example 2. No sufficient polishing effect was achieved.

From the above, it was confirmed that Examples 1 and 2 (Ex1 and Ex2) were able to achieve highest effect compared to Comparative Examples 1 to 4 (Comp1 to Comp4). As presented in Table 1, in Examples 1 and 2, compared to Comparative Examples 1 to 4, the sufficient polishing effect (the degree of gloss) can be achieved. According to the dental polishing instrument of the present invention, the aesthetics can be further improved compared to the traditional polishing instrument in polishing the dental composite resin.

TABLE 1

Compositions of Examples and Comparative Examples, and Evaluation Results of Their Polishing Property and Elasticity

| | Ex1 | Ex2 | Comp1 | Comp2 | Comp3 | Comp4 |
|---|---|---|---|---|---|---|
| Polishing abrasive grains | | | White fused alumina | | | |
| Binder resin | | | Polyester-based resin | | | |
| Base material | | | PET (Polyethylene-terephthalate) | | | |

TABLE 1-continued

Compositions of Examples and Comparative Examples,
and Evaluation Results of Their Polishing Property and Elasticity

|  | Ex1 | Ex2 | Comp1 | Comp2 | Comp3 | Comp4 |
|---|---|---|---|---|---|---|
| Base material shape | Disc shape ($\phi$12 mm) | | | | | |
| Test piece (material to be polished) | Dental composite resin (Beauty Fill 2, Shofu Inc.) | | | | | |
| Height of protrusions | 42 μm | 60 μm | 100 μm | 10 μm | 42 μm | 42 μm |
| Longer diameter and shorter diameter of protrusions | 42 μm | 60 μm | 100 μm | 10 μm | 42 μm | 42 μm |
| Rate of occupancy by protrusions | 70% | 50% | 70% | 70% | 5% | 95% |
| Degree of gloss Gs | 66.9 | 63.7 | 45.2 | 49.3 | 38.1 | 52.2 |

From these evaluation results, the inventors considered that a dental polishing instrument was able to be manufactured with which a high polishing effect (the degree of gloss) was acquired by optimizing the values of the height h of the protrusions 2, the longer diameter $d_1$ and the shorter diameter $d_2$ of the protrusions 2, and the rate of occupancy by the protrusions 2. Therefore, the inventors conducted evaluation to check the influences on the polishing effect (the degree of gloss) of the height h of the protrusions 2, the longer diameter $d_1$ and the shorter diameter $d_2$ of the protrusions 2, and the rate of occupancy by the protrusions 2.

(4) Evaluation of Degree of Gloss Acquired when Height of Protrusions was Varied To check the influence of the height h of the protrusions 2 on the polishing effect (the degree of gloss), measurement and evaluation were executed for the degree of gloss acquired when the longer diameter $d_1$ and the shorter diameter $d_2$ of the protrusions 2 and the rate of occupancy by the protrusions 2 were each set to be constant and the height h of the protrusions 2 was varied. Examples 3 to 7 (Ex3 to Ex7) and Comparative Examples 5 to 8 (Comp5 to Comp8) were used in the measurement and the evaluation of the degree of gloss.

The dental polishing instruments of Examples 3 to 7 and Comparative Examples 5 to 8 were manufactured using a method same as the manufacture method of the above disc type polishing instrument.

Figure 14:
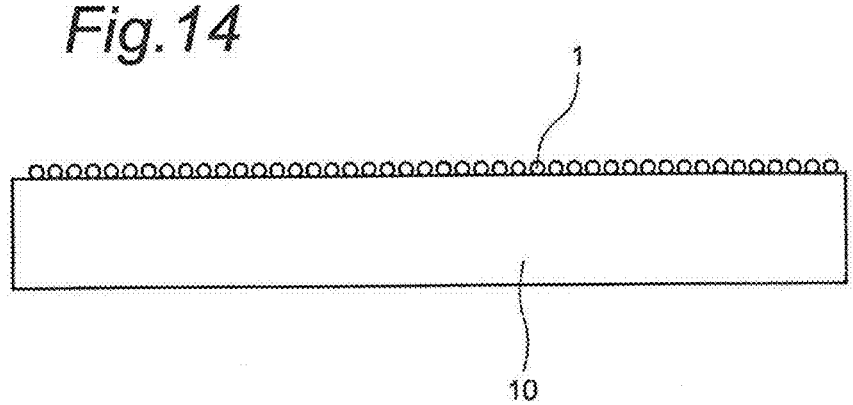
FIG. 14 is a schematic cross-sectional diagram of the polishing layer of a traditional dental polishing instrument.

Examples 3 to 7 and Comparative Examples 6 to 8 were manufactured not varying the longer diameter $d_1$ and the shorter diameter $d_2$ of the protrusions 2 and the rate of occupancy by the protrusions, setting these items to be constant, and varying only the height h of the protrusions 2. Comparative Example 5 was the traditional polishing instrument not including the protrusions 2 in the polishing layer 4 shown in FIG. 14 and was used to compare the polishing effect (the degree of gloss) with those of the polishing instruments each including the protrusions 2.

The manufactured Examples 3 to 7 (Ex3 to Ex7) and Comparative Examples 5 to 8 (Comp5 to Comp8) of the disc type polishing instrument are presented in Table 2. As presented in Table 2, Examples 3 to 7 were manufactured to respectively have the heights h of the protrusions 2 of 20 μm, 42 μm, 60 μm, and 80 μm. In Examples 3 to 7, the longer diameter $d_1$ and the shorter diameter $d_2$ of the protrusions 2 were each set to be 42 μm and the rate of occupancy by the protrusions 2 was set to be 70% per unit area.

Comparative Example 5 was the traditional disc type polishing instrument not including the protrusions 2, and therefore the height h of its protrusions 2 was 0 μm, the longer diameter $d_1$ and the shorter diameter $d_2$ of the protrusions 2 were each 0 μm, and the rate of occupancy by the protrusions 2 was 0%. Comparative Examples 6 to 8 were manufactured whose heights h of the protrusions 2 were respectively 10 μm, 90 μm, and 100 μm. In Comparative Examples 6 to 8, the longer diameter $d_1$ and the shorter diameter $d_2$ of the protrusions 2 were each 42 μm, and the rates of occupancy by the protrusions 2 were each 70% per unit area.

The manufactured disc type polishing instruments of Examples 3 to 7 (Ex3 to Ex7) and Comparative Examples 5 to 8 (Comp5 to Comp8) were each attached to a dedicated mandrel, were each polished the surface of a test piece of a dental composite resin for 30 sec applying a load of about 1 N at 10,000 min$^{-1}$, and the degree of gloss acquired in each of these sessions was evaluated. The test piece was used that was same as the test piece manufactured according to the above procedure. The degree of gloss of the polished surface of the test piece was measured using a mirror gloss degree measurement method of JIS Z 8741.

TABLE 2

|  | Comp5 | Comp6 | Ex3 | Ex4 | Ex5 | Ex6 | Ex7 | Comp7 | Comp8 |
|---|---|---|---|---|---|---|---|---|---|
| Polishing abrasive grains | White fused alumina | | | | | | | | |
| Binder resin | Polyester-based resin | | | | | | | | |
| Base material | PET (Polyethylene-terephthalate) | | | | | | | | |
| Base material shape | Disc shape ($\phi$12 mm) | | | | | | | | |
| Test piece (material to be polished) | Dental composite resin (Beauty Fill 2, Shofu Inc.) | | | | | | | | |
| Height of protrusions | 0 μm | 10 μm | 20 μm | 42 μm | 50 μm | 60 μm | 80 μm | 90 μm | 100 μm |
| Longer diameter and shorter diameter of protrusions | 0 μm | | | | 42 μm | | | | |
| Rate of occupancy by protrusions | 0% | | | | 70% | | | | |
| Degree of gloss Gs | 35.4 | 45.6 | 57.2 | 66.9 | 67.5 | 56.4 | 54.4 | 46.9 | 46.5 |

The polishing effect (the degree of gloss) acquired when the height h of the protrusions 2 was varied is described with reference to Table 2 and FIG. 11.

Figure 11:
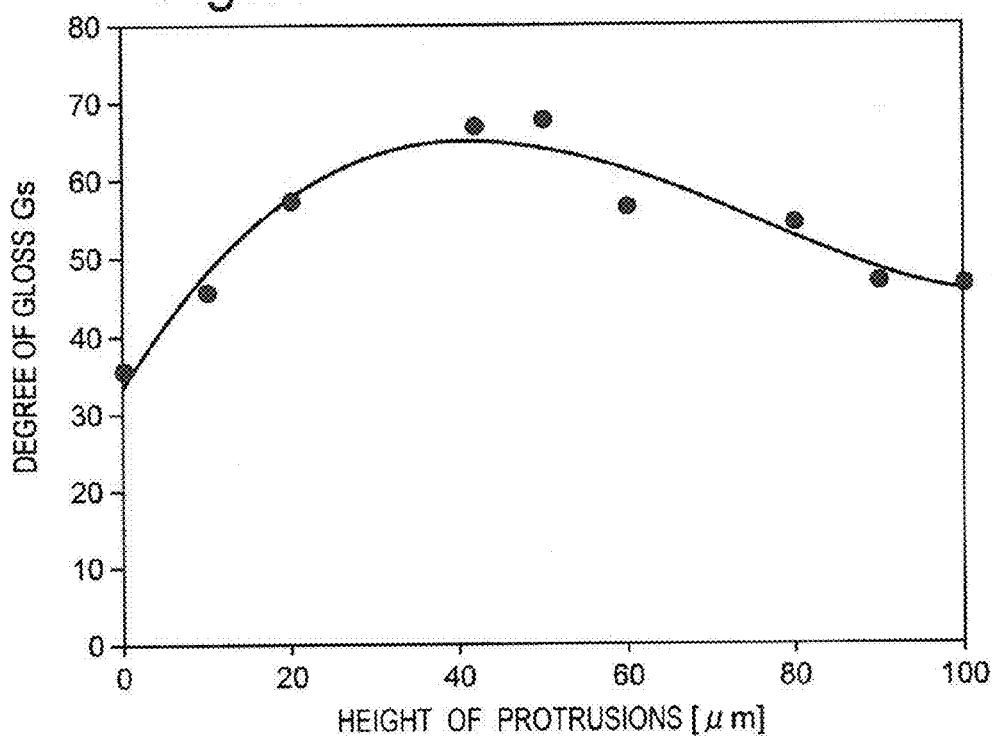
FIG. 11 is a diagram of evaluation results of a degree of gloss acquired when the height is varied of the protrusions of the polishing layer of the dental polishing instrument according to the present invention.

FIG. 11 shows the results of the degrees of gloss acquired when the height h of the protrusions 2 of the polishing layer 4 was varied.

The traditional polishing instrument including no protrusions 2 as shown by Comparative Example 5 (Comp5) is first compared with the polishing instruments each including the protrusions 2 as shown by Examples 3 to 7 (Ex3 to Ex7) and Comparative Examples 6 to 8 (Comp6 to Comp8). As presented in Table 2, compared to the traditional polishing instrument (Comparative Example 5), the polishing instruments each including the protrusions 2 (Examples 3 to 7 and Comparative Examples 6 to 8) each had a higher degree of gloss. The disposition of the protrusions 2 on the polishing layer 4 therefore enables the polishing effect (the degree of gloss) to be improved. When Examples 3 to 7 are compared with Comparative Examples 6 to 8, the degrees of gloss in Examples 3 to 7 were higher than those of Comparative Examples 6 to 8. For example, as shown in FIG. 11, a region for the degree of gloss to have a peak is present in a range from 20 µm to 80 µm of the height h of the protrusions 2. The polishing instruments whose heights h of the protrusions 2 were 20 µm to 80 µm had higher degrees of gloss compared to those of the polishing instruments whose heights h of the protrusions 2 were lower than 20 µm or higher than 80 µm.

The cases are described where the height h of the protrusions 2 was lower than 20 µm (Comparative Example 6) and where the heights h thereof were higher than 80 µm (Comparative Examples 7 and 8). When the height h of the protrusions 2 was lower than 20 µm, the sludge produced during the polishing entered spaces among the protrusions 2 and caused clogging. The polishing instrument whose height h of the protrusions 2 was lower than 20 µm therefore could not achieve any sufficient polishing effect. When the height h of the protrusions 2 was higher than 80 µm, the contact area between the test piece and the protrusions 2 was small. Therefore, the polishing instruments whose heights h of the protrusions 2 were higher than 80 µm could not achieve any sufficient polishing effect.

The cases are described where the heights h of the protrusions 2 were from 20 µm to 80 µm (Examples 3 to 7).

When the height h of the protrusions 2 was from 20 µm to 80 µm, the clogging was suppressed and the contact area was able to be taken to be large between the test piece and the protrusions 2. Therefore, the polishing instruments whose heights h of the protrusions 2 were from 20 µm to 80 µm were each able to achieve sufficient polishing effect compared to Comparative Examples 5 to 8.

As above, the polishing instruments according to the present invention each including the protrusions 2 (Example 3 to 7) were each able to improve the polishing effect (the degree of gloss) achieved for the dental composite resin than the traditional polishing instrument including no protrusions 2 (Comparative Example 5). Therefore, compared to the traditional polishing instrument, the dental polishing instrument according to the present invention can polish a dental composite resin with high aesthetics.

As shown in FIG. 11, since the region for the degree of gloss to have a peak is present in the range from 20 µm to 80 µm of the height h of the protrusions 2, preferably, the height h of the protrusions 2 of the polishing layer 4 of the dental polishing instrument according to the present invention is from 20 µm to 80 µm and, more preferably, is from 35 µm to 50 µm.

(5) Evaluation of Degree of Gloss Acquired when Longer Diameter and Shorter Diameter of Protrusions were Varied To check the influences of the longer diameter $d_1$ and the shorter diameter $d_2$ on the polishing effect (the degree of gloss), measurement and evaluation were executed for the degree of gloss acquired when the height h of the protrusions 2 and the rate of occupancy by the protrusions 2 were set to be constant and the longer diameter $d_1$ and the shorter diameter $d_2$ of the protrusions 2 were varied. Examples 8 to 13 (Ex8 to Ex13) and Comparative Examples 9 and 10 (Comp9 and Comp10) were used in the measurement and the evaluation of the degree of gloss.

The dental polishing instruments of Examples 8 to 13 and Comparative Examples 9 and 10 were manufactured using a method same as the manufacture method of the above disc type polishing instrument.

Examples 8 to 13 and Comparative Examples 9 and 10 were manufactured not varying the height h of the protrusions 2 and the rate of occupancy by the protrusions 2, setting these items to be constant, and varying only the longer diameter $d_1$ and the shorter diameter $d_2$ of the protrusions 2.

The manufactured Examples 8 to 13 (Ex8 to Ex13) and Comparative Examples 9 and 10 (Comp9 and Comp10) of the disc type polishing instrument are presented in Table 3. Comparative Example 5 as shown by Comp5 (the traditional disc type polishing instrument including no protrusion 2 shown in FIG. 14) is presented in Table 3 as a reference. As presented in Table 3, Examples 8 to 13 were manufactured to respectively have the longer diameter $d_1$ and the shorter diameter $d_2$ of the protrusions 2 set to be 20 µm, 42 µm, 50 µm, 60 µm, 80 µm, and 100 µm. In Examples 8 to 13, the height h of the protrusions 2 was set to be 42 µm and the rate of occupancy by the protrusions 2 was set to be 70% per unit area.

Comparative Examples 9 and 10 were manufactured to each have the longer diameter $d_1$ and the shorter diameter $d_2$ of the protrusions 2 respectively set to be 10 µm and 120 µm. In Comparative Examples 9 and 10, the height h of the protrusions 2 was set to be 42 µm and the rate of occupancy by the protrusions 2 was set to be 70% per unit area.

The degree of gloss was evaluated for each of Examples 8 to 13 and Comparative Examples 9 and 10 using the same evaluation method and the same test piece as those used in the evaluation of the degree of gloss acquired when the height h of the protrusions 2 was varied.

TABLE 3

| | Comp5 | Comp9 | Ex8 | Ex9 | Ex10 | Ex11 | Ex12 | Ex13 | Comp10 |
|---|---|---|---|---|---|---|---|---|---|
| Polishing abrasive grains | | | | | White fused alumina | | | | |
| Binder resin | | | | | Polyester-based resin | | | | |
| Base material | | | | | PET (Polyethylene-terephthalate) | | | | |

TABLE 3-continued

|  | Comp5 | Comp9 | Ex8 | Ex9 | Ex10 | Ex11 | Ex12 | Ex13 | Comp10 |
|---|---|---|---|---|---|---|---|---|---|
| Base material shape | Disc shape (φ12 mm) | | | | | | | | |
| Test piece (material to be polished) | Dental composite resin (Beauty Fill 2, Shofu Inc.) | | | | | | | | |
| Height of protrusions | 0 μm | | | | 42 μm | | | | |
| Longer diameter and shorter diameter of protrusions | 0 μm | 10 μm | 20 μm | 42 μm | 50 μm | 60 μm | 80 μm | 100 μm | 120 μm |
| Rate of occupancy by protrusions | 0% | | | | 70% | | | | |
| Degree of gloss Gs | 35.4 | 45.2 | 60.2 | 66.9 | 65.4 | 64.6 | 59.9 | 56.4 | 51.3 |

The polishing effect (the degree of gloss) acquired when the longer diameter $d_1$ and the shorter diameter $d_2$ of the protrusions 2 were varied is described with reference to Table 3 and FIG. 12.

Figure 12:
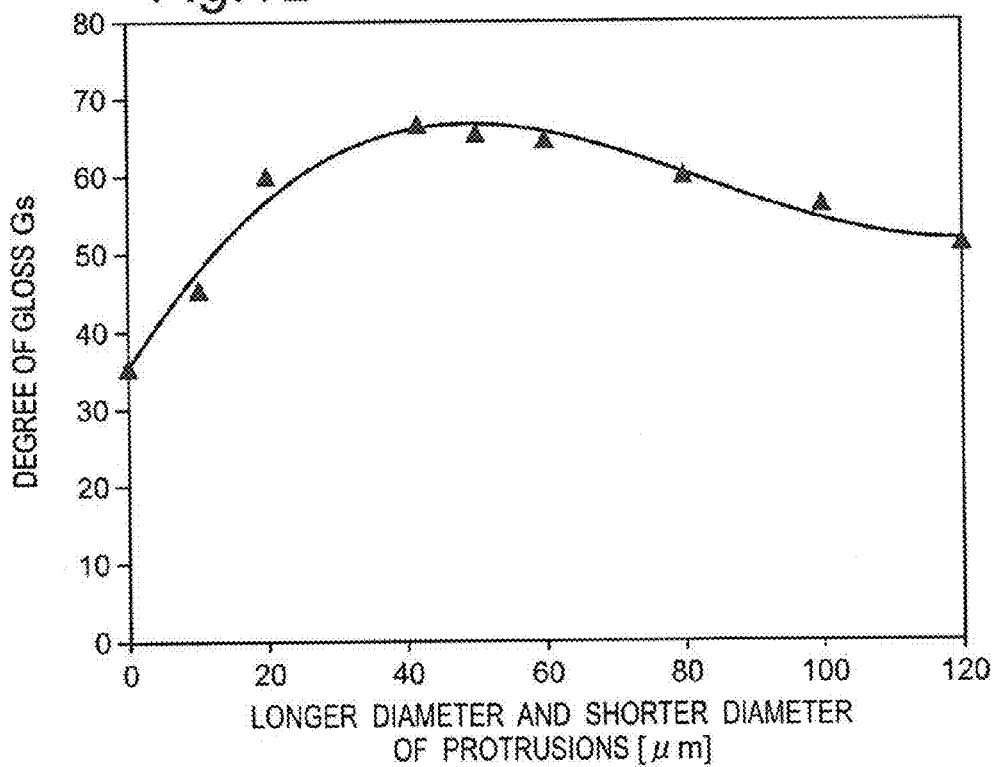
FIG. 12 is a diagram of evaluation results of the degree of gloss acquired when the longer diameter and the shorter diameter are varied of the protrusions of the polishing layer of the dental polishing instrument according to the present invention.

FIG. 12 shows the results of the degrees of gloss acquired when the longer diameter $d_1$ and the shorter diameter $d_2$ of the protrusions 2 of the polishing layer 4 were varied.

As presented in Table 3, when Examples 8 to 13 (Ex8 to Ex13) are compared with Comparative Examples 5, 9, and 10 (Comp5, Comp9, and Comp10), the degrees of gloss of Examples 8 to 13 were higher than those of Comparative Examples 5, 9, and 10. For example, as shown in FIG. 12, a region for the degree of gloss to have a peak is present in a range from 20 μm to 100 μm of the longer diameter $d_1$ and the shorter diameter $d_2$ of the protrusions 2. Therefore, the polishing instruments whose longer diameter $d_1$ and shorter diameter $d_2$ of the protrusions 2 were from 20 μm to 100 μm had higher degrees of gloss compared to those of the polishing instruments whose longer diameter $d_1$ and shorter diameter $d_2$ of the protrusions 2 were shorter than 20 μm, or longer than 100 μm.

The cases are described where the longer diameter $d_1$ and the shorter diameter $d_2$ of the protrusions 2 were shorter than 20 μm (Comparative Examples 5 and 9) and where the diameters $d_1$ and $d_2$ were longer than 100 μm (Comparative Example 10).

When the longer diameter $d_1$ and the shorter diameter $d_2$ of the protrusions 2 were shorter than 20 μm, the contact area between the test piece and the protrusions 2 was small. Therefore, the polishing instruments whose longer diameter $d_1$ and shorter diameter $d_2$ of the protrusions 2 were shorter than 20 μm could not achieve any sufficient polishing effect. When the longer diameter $d_1$ and the shorter diameter $d_2$ of the protrusions 2 were longer than 120 μm, the sludge produced during the polishing entered interspaces among the protrusions 2 and caused clogging. The polishing instruments whose longer diameter $d_1$ and shorter diameter $d_2$ of the protrusions 2 were longer than 120 μm therefore could not achieve any sufficient polishing effect.

The case is described where the longer diameter $d_1$ and the shorter diameter $d_2$ of the protrusions 2 were from 20 μm to 100 μm (Example 8 to 13).

When the longer diameter $d_1$ and the shorter diameter $d_2$ of the protrusions 2 were from 20 μm to 100 μm, the clogging was suppressed and the contact area was able to be taken to be large between the test piece and the protrusions 2. Therefore, the polishing instruments whose longer diameter $d_1$ and shorter diameter $d_2$ of the protrusions 2 were from 20 μm to 100 μm were each able to achieve a sufficient polishing effect.

As above, since the region for the degree of gloss to have the peak is present in a range from 20 μm to 100 μm of the longer diameter $d_1$ and the shorter diameter $d_2$ of the protrusions 2 (Examples 8 to 13), preferably, the longer diameter $d_1$ and the shorter diameter $d_2$ of the protrusions 2 of the polishing layer 4 of the dental polishing instrument according to the present invention are from 20 μm to 100 μm and, more preferably, are from 30 μm to 70 μm.

(6) Evaluation of Degree of Gloss Acquired when Rate of Occupancy by Protrusions was Varied To check the influence of the rate of occupancy by the protrusions 2 on the polishing effect (the degree of gloss), measurement and evaluation were executed for the degree of gloss acquired when the height h of the protrusions 2 and the longer diameter $d_1$ and the shorter diameter $d_2$ of the protrusions 2 were set to be constant and the rate of occupancy by the protrusions 2 was varied. Examples 14 to 18 (Ex14 to Ex18) and Comparative Examples 11 to 13 (Comp11 to Comp13) were used in the measurement and the evaluation of the degree of gloss.

The dental polishing instruments of Examples 14 to 18 and Comparative Examples 11 to 13 were manufactured using the method same as the manufacture method of the above disc type polishing instrument.

Examples 14 to 18 and Comparative Examples 11 to 13 were manufactured not varying the height h of the protrusions 2 and the longer diameter $d_1$ and the shorter diameter $d_2$ of the protrusions 2, setting these items to be constant, and varying only the rate of occupancy by the protrusions.

The manufactured Examples 14 to 18 and Comparative Examples 11 to 13 of the disc type polishing instrument are presented in Table 4. Comparative Example 5 as shown by Comp5 (the traditional disc type polishing instrument including no protrusion 2 shown in FIG. 14) is presented in Table 4 as the reference. As presented in Table 4, Examples 14 to 18 were manufactured to respectively have the rate of occupancy by the protrusions 2 of 40%, 50%, 70%, 80%, and 90%. In Examples 14 to 18, the height h of the protrusions 2 was set to be 42 μm, and the longer diameter $d_1$ and the shorter diameter $d_2$ of the protrusions 2 were each set to be 42 μm.

Comparative Examples 11 to 13 were manufactured whose rates of occupancy by the protrusions 2 were respectively 5%, 20%, and 95%. In Comparative Examples 11 to 13, the height h of the protrusions 2 was set to be 42 μm and the longer diameter $d_1$ and the shorter diameter $d_2$ of the protrusions 2 were each set to be 42 μm.

The degree of gloss was evaluated for each of Examples 14 to 18 and Comparative Examples 11 to 13 using the same evaluation method and the same test piece as those used in the evaluation of the degree of gloss acquired when the rate of occupancy by the protrusions 2 was varied.

TABLE 4

| | Comp5 | Comp11 | Comp12 | Ex14 | Ex15 | Ex16 | Ex17 | Ex18 | Comp13 |
|---|---|---|---|---|---|---|---|---|---|
| Polishing abrasive grains | | | | White fused alumina | | | | | |
| Binder resin | | | | Polyester-based resin | | | | | |
| Base material | | | | PET (Polyethylene-terephthalate) | | | | | |
| Base material shape | | | | Disc shape (φ12 mm) | | | | | |
| Test piece (material to be polished) | | | | Dental composite resin (Beauty Fill 2, Shofu Inc.) | | | | | |
| Height of protrusions | 0 μm | | | 42 μm | | | | | |
| Longer diameter and shorter diameter of protrusions | 0 μm | | | 42 μm | | | | | |
| Rate of occupancy by protrusions | 0% | 5% | 20% | 40% | 50% | 70% | 80% | 90% | 95% |
| Degree of gloss Gs | 35.4 | 30.8 | 35.4 | 60.5 | 65.1 | 66.9 | 65.5 | 60.8 | 52.2 |

The polishing effect acquired when the rate of occupancy by the protrusions 2 was varied is described with reference to Table 4 and FIG. 13.

Figure 13:
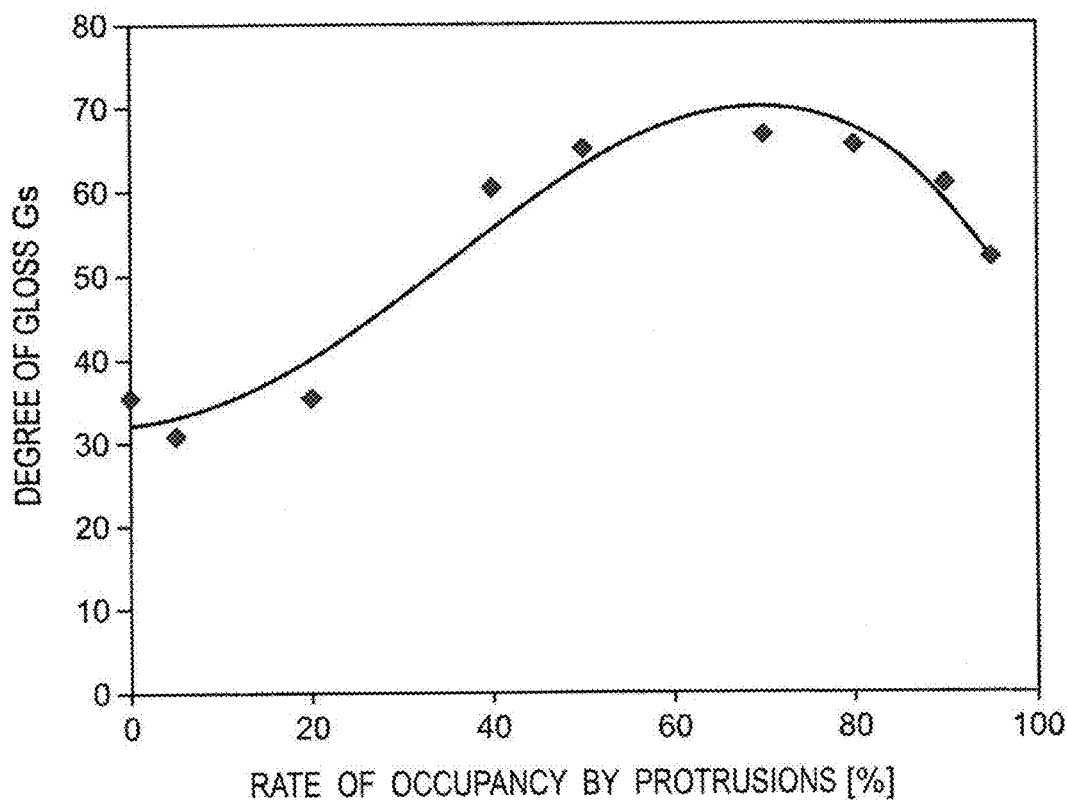
FIG. 13 is a diagram of evaluation results of the degree of gloss acquired when the rate of occupancy by the protrusions is varied in the polishing layer of the dental polishing instrument according to the present invention.

FIG. 13 shows evaluation results of the degree of gloss acquired when the rate of occupancy by the protrusions 2 of the polishing layer 4 was varied.

When Examples 14 to 18 (Ex14 to Ex18) are compared with Comparative Examples 5 and 11 to 13 (Comp5, and Comp11 to Comp13), the degrees of gloss of Examples 14 to 18 were higher than those of Comparative Examples 5 and 11 to 13. For example, as shown in FIG. 13, a region for the degree of gloss to have a peak is present in a range from 40% to 90% per unit area of the rate of occupancy by the protrusions 2. Therefore, the polishing instruments whose rates of occupancy by the protrusions 2 were 40% to 90% per unit area had higher degrees of gloss compared to those of the polishing instruments whose rate of occupancy by the protrusions 2 was smaller than 40% or the polishing instruments whose rate of occupancy by the protrusions 2 was greater than 90%.

The cases are described where the rates of occupancy by the protrusions 2 were lower than 40% per unit area (Comparative Examples 5, 11, and 12) and where the rate of occupancy by the protrusions 2 was higher than 90% per unit area (Comparative Example 13).

When the rate of occupancy by the protrusions 2 was lower than 40% per unit area, the contact area between the test piece and the protrusions 2 was small. Therefore, the polishing instrument whose rate of occupancy by the protrusions 2 was lower than 40% per unit area could not achieve any sufficient polishing effect. When the rate of occupancy by the protrusions 2 was higher than 90% per unit area, sufficient interspace could not be formed with the protrusions 2 and clogging occurred during the polishing. Therefore, the polishing instruments whose rate of occupancy by the protrusions 2 was higher than 90% per unit area could not achieve any sufficient polishing effect.

The cases are described where the rate of occupancy by the protrusions 2 was from 40% to 90% per unit area (Examples 14 to 18).

When the rate of occupancy by the protrusions 2 was from 40% to 90% per unit area, the clogging was suppressed and the contact area was able to be taken to be large between the test piece and the protrusions 2. The polishing instruments whose rate of occupancy by the protrusions 2 was from 40% to 90% per unit area were each able to achieve a sufficient polishing effect.

As above, since the region for the degree of gloss to have the peak is present in the range from 40% to 90% per unit area of the rate of occupancy by the protrusions 2 as shown by Examples 14 to 18 (Ex14 to Ex18), preferably, the rate of occupancy by the protrusions 2 of the polishing layer 4 of the dental polishing instrument according to the present invention is from 40% to 90% per unit area and, more preferably, is 50% to 80%.

Second Embodiment

In the second embodiment, the case is described where a dental porcelain is polished using the point type polishing instrument.

Examples of the point type polishing instrument are described below.

(1) Manufacture Method

Examples and Comparative Examples of the point type polishing instrument were manufactured as below.

For the polishing layer 4, the polishing abrasive grains 1 and the binder resin 3 were mixed at the blending ratios of 50%:50%. In this case, artificial diamond was used as the polishing abrasive grains 1 and their particle diameter was set to be #2000. A polyester-based resin material was employed as the binder resin 3. A dilution solvent and a hardening agent were in addition blended. The blending was executed to set the practical blending ratios to be 100 weight parts of the polyester-based resin, 75 weight parts of the dilution solvent, 5 weight parts of hardening agent, and 100 weight parts of the artificial diamond. The mixture was applied to the mold sheet (the mold) manufactured in advance and including plural point-shaped recesses using the top reverse coater (the coating machine) and was hardened. After the hardening, the polishing layer 4 was detached from the mold sheet and, thereby, the final polishing layer 4 was acquired. A silicon resin was employed as the elastomer-based binder and a piece thereof shaped into a bullet shape having the largest diameter of 5 mm and a height of 13 mm using hot pressing was used as the point-shaped base material 6. A blended solution including 100 weight parts of a polyurethane-based resin and 5 weight parts of a modified polyisocyanate resin as the hardening agent was applied to the point-shaped base material 6 and was dried using a hot air dryer to form the primer layer on the point-shaped base material 6. The polishing layer 4 and the point-shaped base material 6 having the primer layer formed thereon were brought into contact with each other, and hot pressing was applied thereto to fix the polishing layer 4 and the point-shaped base material 6 to each other.

(2) Examples and Comparative Examples

The manufactured Examples and Comparative Examples of the point type polishing instrument are presented in Table 5.

(3) Evaluation Method of Surface Roughness

The evaluation of the surface roughness was employed as the evaluation method of the polishing property and the elasticity acquired when the point type polishing instrument was attached to a dedicated mandrel and polished the surface of a test piece of a porcelain for 30 sec applying a load of about 1 N at 15,000 $min^{-1}$.

The test piece was manufactured according to the following procedure. Powder of a dental porcelain (Vintage MP, Shofu Inc.) and distilled water were mixed to acquire slurry, and the slurry was put in a silicon mold for $\phi$ (diameter) of 15 mm and a thickness of 2 mm to remove moisture therefrom using a condensing method. Thereafter, the molded piece was taken out from the mold. The taken out molded piece was sintered in a baking furnace using a usual manner and the roughness of the surface was set to be a specific roughness using a water resistant polishing paper sheet of #400 to acquire a specimen.

The surface roughness of the polished surface of the test piece was measured according to a JIS B 0633 product geometrical property specification.

TABLE 5

Compositions of Examples and Comparative Examples, and Evaluation Results of Their Polishing Property and Elasticity

|  | Ex19 | Ex20 | Comp14 | Comp15 | Comp16 | Comp17 |
|---|---|---|---|---|---|---|
| Polishing abrasive grains | White fused alumina | | | | | |
| Binder resin | Polyester-based resin | | | | | |
| Base material | Urethane rubber | | | | | |
| Base material shape | Bullet shape (Diameter: 5 mm, Height: 13 mm) | | | | | |
| Test piece (material to be polished) | Dental porcelain (Vintage MP, Shofu Inc.) | | | | | |
| Height of protrusions | 42 μm | 60 μm | 100 μm | 10 μm | 42 μm | 42 μm |
| Longer diameter and shorter diameter of protrusions | 42 μm | 60 μm | 100 μm | 10 μm | 42 μm | 42 μm |
| Rate of occupancy by protrusions | 70% | 50% | 70% | 70% | 5% | 95% |
| Surface roughness Ra [μm] | 0.189 | 0.201 | 0.402 | 0.423 | 0.450 | 0.308 |

Relative to Examples 19 and 20 (Ex19 and Ex20), in Comparative Example 14 (Comp14), the height h of the protrusions 2 was high and the longer diameter $d_1$ and the shorter diameter $d_2$ were long. Therefore, no clogging occurred while the contact area was small and no sufficient polishing effect was achieved. In Comparative Example 15 (Comp15), the height h of the protrusions was low and the longer diameter $d_1$ and the shorter diameter $d_2$ were short. Therefore, the sludge produced during the polishing caused clogging and no sufficient polishing effect was achieved compared to Examples 19 and 20.

In Comparative Example 16 (Comp16), the rate of occupancy by the protrusions 2 was low and the area to be in contact with the polished surface was small and no sufficient polishing effect was achieved.

In Comparative Example 17 (Comp17), the rate of occupancy by the protrusions 2 was high and no sufficient interspaces were acquired. Therefore, clogging occurred during the polishing similarly to Comparative Example 15 and no sufficient polishing effect was achieved.

From the above, it was confirmed that Examples 19 and 20 each achieved the highest effect compared to Comparative Examples 14 to 17. As presented in Table 5, in Examples 19 and 20 (Ex19 and Ex20), the surface roughness is low compared to Comparative Examples 14 to 17 (Comp14 to Comp17), and the dental polishing instrument according to the present invention can achieve sufficient polishing effect for a dental porcelain.

Third Embodiment

In the third embodiment, Examples are described for the case where a dental composite resin is polished using the sheet type polishing instrument.

Examples of the sheet type polishing instrument are described below.

(1) Manufacture of Sheet Type Polishing Instrument

Examples and Comparative Examples of the sheet type polishing instrument were manufactured as below.

For the polishing layer 4, the polishing abrasive grains 1 and the binder resin 3 were mixed at the blending ratios of 50%:50%. In this case, white fused alumina was used as the polishing abrasive grains 1 and their particle diameter was set to be #1000. A polyester-based resin material was employed as the binder resin 3. A dilution solvent and a hardening agent were in addition blended. The blending was executed to set the practical blending ratios to be 100 weight parts of the polyester-based resin, 75 weight parts of the dilution solvent, 5 weight parts of the hardening agent, and 100 weight parts of the white fused alumina. The mixture was applied to the mold sheet (the mold) manufactured in advance and including a sheet-shaped recess using the top reverse coater (the coating machine) and was hardened. After the hardening, the polishing layer 4 was detached from the mold sheet and, thereby, the final polishing layer 4 was acquired. A rectangular shaped polyethylene-terephthalate (PET) piece having a thickness of 0.25 mm, a shorter side length of 5 mm, and a longer side length of 150 mm was used as the sheet-shaped base material 7. A blended solution including 100 weight parts of a polyurethane-based resin and 5 weight parts of a modified polyisocyanate resin as the hardening agent was applied to the PET piece and was dried using a hot air dryer to form the primer layer having a thickness of about 0.05 mm on the sheet-shaped base material 7. The overall thickness of this sheet-shaped base material 7 was 0.875 μm including that of the primer layer. The polishing layer 4 and the sheet-shaped base material 7 having the primer layer formed thereon were brought into contact with each other, and hot pressing was applied thereto to fix the polishing layer 4 and the sheet-shaped base material 7 to each other to acquire the sheet type polishing instrument.

(2) Examples and Comparative Examples

The manufactured Examples and Comparative Examples of the sheet type polishing instrument are presented in Table 6.

Settings were made in Example 21 (Ex21), for the height h of the protrusions 2 to be 42 μm, for the longer diameter $d_1$ and the shorter diameter $d_2$ of the protrusions 2 to be 42 μm, for the shape of the protrusion 2 to be a semispherical body, and for the rate of occupancy by the protrusions 2 to be 70% per unit area. Settings were made in Example 22 (Ex22), for the height h of the protrusions 2 to be 60 μm, for the longer diameter $d_1$ and the shorter diameter $d_2$ of the protrusions 2 to be 60 μm, for the shape of the protrusion 2 to be a semispherical body, and for the rate of occupancy by the protrusions 2 to be 50% per unit area. Comparative Examples 18 to 21 (Comp18 to Comp21) were manufactured using the same manufacture method as above.

(3) Evaluation Method of Surface Roughness

The evaluation of the surface roughness was executed that was acquired when the manufactured sheet type polishing instrument was brought into contact with the surface of the test piece of the dental composite resin and, in this state, the test pieces was polished for 30 sec being caused to make reciprocal motions under a load of about 1 N. The test piece was manufactured according to the following procedure. A stainless ring having an inner diameter of 15 mm and a thickness of 2 mm was placed on a glass slide, and a dental composite resin (Beauty Fill 2, Shofu Inc.) was poured to fill the ring. Another glass slide was further placed thereon and polymerization was executed from both sides for 3 min using a dental optical polymerization vessel (Twincure, Shofu Inc.) and the roughness of the surfaces was set to be a specific roughness using a water resistant polishing paper sheet of #600 to acquire a cylindrical test piece. The surface roughness of the polished surface of the test piece was measured according to a JIS B 0633 product geometrical property specification.

Relative to Examples 21 and 22 (Ex21 and Ex22), in Comparative Example 18 (Comp18), the height h of the protrusions 2 was high and the longer diameter $d_1$ and the shorter diameter $d_2$ were long. Therefore, no clogging occurred. However, the contact area was small between the polishing layer 4 and the test piece and the test piece was excessively ground. Therefore, no sufficient polishing effect was achieved. In Comparative Example 19 (Comp19), the height h of the protrusions 2 was low and the longer diameter $d_1$ and the shorter diameter $d_2$ were short. Therefore, the sludge produced during the polishing caused clogging and no sufficient polishing effect was achieved compared to Examples 21 and 22.

In Comparative Example 20 (Comp20), the rate of occupancy by the protrusions 2 was low and the area to be in contact with the polished surface was small. Therefore, no sufficient polishing effect was achieved.

In Comparative Example 21 (Comp21), the rate of occupancy by the protrusions 2 was high and no sufficient interspaces were acquired. Therefore, clogging was occurred during the polishing similarly to Comparative Example 19 and no sufficient polishing effect was achieved.

From the above, it was confirmed that Examples 21 and 22 each achieved the highest effect compared to Comparative Examples 18 to 21. As presented in Table 6, in Examples 21 and 22, the surface roughness was low compared to Comparative Examples 19 to 21, and the dental polishing instrument according to the present invention can achieve sufficient polishing effect for a dental composite resin.

TABLE 6

Compositions of Examples and Comparative Examples, and Evaluation Results of Their Polishing Property and Elasticity

| | Ex21 | Ex22 | Comp18 | Comp19 | Comp20 | Comp21 |
|---|---|---|---|---|---|---|
| Polishing abrasive grains | White fused alumina | | | | | |
| Binder resin | Polyester-based resin | | | | | |
| Base material | PET (Polyethylene-terephthalate) | | | | | |
| Base material shape | Rectangular shape (Shorter side length: 5 mm × Longer side length: 150 mm) | | | | | |
| Test piece (material to be polished) | Dental composite resin (Beauty Fill 2, Shofu Inc.) | | | | | |
| Height of protrusions | 42 μm | 60 μm | 100 μm | 10 μm | 42 μm | 42 μm |
| Longer diameter and shorter diameter of protrusions | 42 μm | 60 μm | 100 μm | 10 μm | 42 μm | 42 μm |
| Rate of occupancy by protrusions | 70% | 50% | 70% | 70% | 5% | 95% |
| Surface roughness Ra [μm] | 0.154 | 0.182 | 0.352 | 0.373 | 0.400 | 0.278 |

As above, the dental polishing instrument according to the present invention has the protrusions 2 disposed in the polishing layer 4. The protrusions 2 of the polishing layer 4 are each independently formed being raised in the surface direction that is the direction toward the object to be polished. For example, the height h of the protrusions 2 is 20 μm to 80 μm, and the longer diameter $d_1$ and the shorter diameter $d_2$ of the protrusions 2 are 20 μm to 100 μm. As to each of the protrusions 2, for example, the length of the shorter diameter is 80 to 100% relative to the length of the longer diameter. The rate of occupancy by the protrusions 2 per unit area in the polishing layer 4 is, for example, 40 to 90%. The protrusions 2 may regularly be disposed on the surface of the polishing layer 4 or may randomly be disposed thereon.

It has been described that, with the above configuration, when the dental polishing instrument of the first embodiment according to the present invention polishes a dental composite resin, the dental polishing instrument can achieve a sufficient polishing effect (the degree of gloss) compared to the traditional dental polishing instrument. The "dental composite resin" includes a glass filler having high hardness and a resin having low hardness. The dental polishing instrument of the present invention has been described using the dental composite resin as the material to be polished while the material is not limited to this. The dental polishing instrument can polish, for example, a porcelain and a metal included in a dental prosthetic appliance.

The present invention has been described in a degree of detail in the embodiments. However, the content of the disclosure of these embodiments may naturally vary in the detailed configuration, and changes can be realized to the combination and order of elements in the embodiments without departing from the scope and the idea of claims.

INDUSTRIAL APPLICABILITY

The dental polishing instrument according to the present invention can suppress clogging and occurrence of any secondary flaw due to the polishing sludge and can efficiently polish by forming a polishing abrasive grain layer including polishing abrasive grains and a resin material, into protrusions on the surface of the base material of the polishing instrument and by regularly disposing the protrusions on the base material.

REFERENCE SIGNS LIST 1 polishing abrasive grain
2 protrusion
3 binder resin
4 polishing layer
5 disc-shaped base material
6 point-shaped base material
7 rectangular shaped base material
8 shaft
9 soft block
10 base material
11 non-protruding portion
20 dental prosthetic appliance
21 natural tooth
30 mold sheet (a mold)
31 recess

The invention claimed is:

1. A dental polishing instrument comprising:
a base material forming a mother body;
a polishing layer disposed on a surface of the base material; and
protrusions that are disposed on a surface of the polishing layer,
wherein the protrusions are each formed independently from each other,
wherein each of the protrusions has a height of 20 μm to 80 μm, and has an oval shape when viewed from the top thereof,
wherein each of the protrusions includes polishing abrasive grains mounted thereon,
wherein a length of a longer diameter and a shorter diameter of the oval shape of each of the protrusions is 20 μm to 100 μm, and the length of the shorter diameter is 80% to 100% of the length of the longer diameter, and
wherein a rate of occupancy of the protrusions per unit area in the polishing layer is 40% to 90%.

2. The dental polishing instrument of claim 1, further comprising non-protruding portions between the protrusions that have no protrusion formed thereon, on the surface of the polishing layer,
wherein the non-protruding portions are contiguously connected to each other.

3. The dental polishing instrument of claim 1,
wherein the polishing layer comprises polishing abrasive grains and a binder resin,
wherein the polishing abrasive grains comprise one or more compounds selected from alumina, zirconia, silicon carbide, diamond, silica, calcium carbonate, cerium oxide, and boron nitride, and have granularity of #400 to #8000 at a content of 30 to 90 weight parts relative to 100 weight parts of the polishing layer, and
wherein the binder resin comprises one or more resins selected from polyester-based resins, epoxy-based resins, and polyurethane-based resins at a content of 10 to 70 weight parts relative to 100 weight parts of the polishing layer.

4. The dental polishing instrument of claim 3, wherein the protrusions comprise a mixture of the polishing abrasive grains and the binder resin.

5. The dental polishing instrument of claim 1, wherein the base material has a disc shape with a diameter of 4 mm to 16 mm and a thickness of 0.050 mm to 0.150 mm, and has the polishing layer on its one flat surface, and also has a connecting portion for connecting to a shaft of a driver.

6. The dental polishing instrument of claim 5, wherein another polishing layer is disposed on another surface of the disc-shaped base material.

7. The dental polishing instrument of claim 1, wherein the base material has a shape of a column body with a front surface and a bottom surface.

8. The dental polishing instrument of claim 1, wherein the base material has a shape of a conical body with a front surface and a bottom surface.

9. The dental polishing instrument of claim 1, wherein the base material has a shape of a parabola revolution body with a front surface and a bottom surface.

10. The dental polishing instrument of claim 1, wherein the base material has a bullet shape with a front surface and a bottom surface.

11. The dental polishing instrument of claim 7, wherein the base material has a largest diameter of 2 mm to 20 mm and a height of 5 mm to 40 mm, has the polishing layer disposed on the front surface, and has a connecting portion for connecting to a shaft of a driver on the bottom surface.

12. The dental polishing instrument of claim 1, wherein the base material has rectangular shape with a shorter side being 1 mm to 10 mm and a longer side being 10 mm to 50 m, and has the polishing layer on one or both surfaces thereof.

* * * * *